(12) United States Patent
Lee et al.

(10) Patent No.: US 11,596,764 B2
(45) Date of Patent: Mar. 7, 2023

(54) ELECTRONIC DEVICE AND METHOD FOR PROVIDING INFORMATION FOR STRESS RELIEF BY SAME

(71) Applicant: Samsung Electronics Co., Ltd., Gyeonggi-do (KR)

(72) Inventors: Donghyun Lee, Gyeonggi-do (KR); Sangbeom Nam, Gyeonggi-do (KR); Hyogil Kim, Gyeonggi-do (KR); Ahram Suh, Gyeonggi-do (KR); Hoon Cho, Gyeonggi-do (KR)

(73) Assignee: Samsung Electronics Co., Ltd

( * ) Notice: Subject to any disclaimer, the term of this patent is extended or adjusted under 35 U.S.C. 154(b) by 243 days.

(21) Appl. No.: 16/844,292

(22) Filed: Apr. 9, 2020

(65) Prior Publication Data

US 2020/0324074 A1 Oct. 15, 2020

(30) Foreign Application Priority Data

Apr. 11, 2019 (KR) .......................... 10-2019-0042557

(51) Int. Cl.
*A61M 21/02* (2006.01)
*G16H 20/70* (2018.01)
(Continued)

(52) U.S. Cl.
CPC ............. *A61M 21/02* (2013.01); *A61B 5/165* (2013.01); *A61B 5/7275* (2013.01); *G16H 20/70* (2018.01);
(Continued)

(58) Field of Classification Search
CPC ........ A61M 2205/332; A61M 2205/18; A61M 2205/3313; A61M 2205/3358;
(Continued)

(56) References Cited

U.S. PATENT DOCUMENTS

2012/0289790 A1  11/2012  Jain et al.
2017/0071523 A1  3/2017  Jain et al.

FOREIGN PATENT DOCUMENTS

JP   2018-011720       1/2018
KR   1020150047158    5/2015
(Continued)

OTHER PUBLICATIONS

S. Kwon, H. Kim and K. S. Park, "Validation of heart rate extraction using video imaging on a built-in camera system of a smartphone," 2012 Annual International Conference of the IEEE Engineering in Medicine and Biology Society, 2012, pp. 2174-2177, doi: 10.1109/EMBC.2012.6346392. (Year: 2012).*

(Continued)

*Primary Examiner* — Thaddeus B Cox
*Assistant Examiner* — Marc D. Honrath
(74) *Attorney, Agent, or Firm* — The Farrell Law Firm, P.C.

(57) ABSTRACT

An electronic device and method for providing information for stress relief are disclosed. The electronic device includes a user interface, at least one sensor, at least one processor operatively connected to the user interface and the at least one sensor, and a memory operatively connected to the at least one processor. The memory stores instructions to, when executed, cause the at least one processor to collect stress-related information through at least a part of the at least one sensor, identify contextual information of a user when stress calculated based on the collected stress-related information satisfies a designated condition, and guide at least one of a plurality of stress relief methods through the user interface at least based on the identified contextual information.

20 Claims, 17 Drawing Sheets

(51) Int. Cl.
*A61B 5/16* (2006.01)
*A61B 5/00* (2006.01)
*A61M 21/00* (2006.01)

(52) U.S. Cl.
CPC .............. *A61M 2021/005* (2013.01); *A61M 2021/0027* (2013.01); *A61M 2205/502* (2013.01); *A61M 2230/06* (2013.01)

(58) Field of Classification Search
CPC .. A61M 2205/3368; A61M 2205/3553; A61M 2205/3569; A61M 2205/3584; A61M 2205/3592; A61M 2205/502; A61M 2205/505; A61M 2205/507; A61M 2205/52; A61M 2205/609; A61M 2205/8206; A61M 2230/04; A61M 2230/06; A61M 2230/201; A61M 2230/205; A61M 2230/30; A61M 2230/50; A61M 2230/62; A61M 2230/63; A61M 2021/0022; A61M 2021/0027; A61M 2021/005; A61M 2209/088; A61B 5/0024; A61B 5/024; A61B 5/165; A61B 5/4884; A61B 5/7275; A61B 5/746; G16H 20/70; G16H 20/63; H04M 1/725
See application file for complete search history.

(56) References Cited

FOREIGN PATENT DOCUMENTS

| | | | |
|---|---|---|---|
| KR | 20170093470 A | * 8/2017 | ............. G04G 21/02 |
| KR | 1020170093470 | 8/2017 | |
| KR | 10-1809131 | 12/2017 | |
| KR | 1020190007803 | 1/2019 | |
| KR | 1020190021113 | 3/2019 | |
| KR | 1020190043319 | 4/2019 | |
| WO | WO 2018/016459 | 1/2018 | |
| WO | WO 2018/084157 | 5/2018 | |
| WO | WO-2019065765 A1 | * 4/2019 | ......... A61B 5/02055 |

OTHER PUBLICATIONS

International Search Report dated Jul. 31, 2020 issued in counterpart application No. PCT/KR2020/004804, 7 pages.
European Search Report dated May 6, 2022 issued in counterpart application No. 20787910.7-1126, 10 pages.
Indian Examination Report dated Mar. 15, 2022 issued in counterpart application No. 202117050735, 9 pages.
Chinese Office Action dated Nov. 25, 2022 issued in counterpart application No. 202080027687.1, 26 pages.

* cited by examiner

ELECTRONIC DEVICE AND METHOD FOR PROVIDING INFORMATION FOR STRESS RELIEF BY SAME

CROSS-REFERENCE TO RELATED APPLICATION(S)

This application is based on and claims priority under 35 U.S.C. 119 to Korean Patent Application No. 10-2019-0042557, filed on Apr. 11, 2019, in the Korean Intellectual Property Office, the entire disclosure of which is incorporated herein by reference.

BACKGROUND

1. Field

The present disclosure relates generally to an electronic device and a method for providing information for stress relief by the electronic device.

2. Description of Related Art

Electronic devices (e.g., a mobile terminal, a smart phone, or a wearable device) may provide various functions and/or services. In addition to a basic voice communication function, a smartphone may provide a short-range wireless communication (e.g., Bluetooth™, Wi-Fi, or near field communication (NFC)) function, a mobile communication ($3^{rd}$ generation (3G), 4G, or 5G) function, a music or video playback function, a photographing function, or a navigation function.

Meanwhile, recent electronic devices provide a health-related service. Recent electronic devices may detect biometric information of a user by using various sensors, and provide various services (e.g., a stress measurement service) by using the detected biometric information (e.g., a heart rate, a blood pressure, etc.).

The electronic devices may only provide a measured stress value. However, when a high stress state is maintained for a predetermined period of time or occurs frequently, it may adversely affect health. Therefore, it is important to relieve stress rather than to simply measure stress.

SUMMARY

The present disclosure has been made to address at least the disadvantages described above and to provide at least the advantages described below.

In accordance with an aspect of the present disclosure, an electronic device is provided. The electronic device includes a user interface, at least one sensor, at least one processor operatively connected to the user interface and the at least one sensor, and a memory operatively connected to the at least one processor. The memory stores instructions to, when executed, cause the at least one processor to collect stress-related information through at least a part of the at least one sensor, identify contextual information of a user when stress calculated based on the collected stress-related information satisfies a designated condition, and guide at least one of a plurality of stress relief methods through the user interface at least based on the identified contextual information.

In accordance with an aspect of the present disclosure, a method for providing information for stress relief by an electronic device is provided. The method includes collecting stress-related information through at least a part of at least one sensor, determining whether stress calculated based on the collected stress-related information satisfies a designated condition, identifying contextual information of a user in response to satisfying of the designated condition, and guiding at least one of a plurality of stress relief methods through a user interface at least based on the identified contextual information.

BRIEF DESCRIPTION OF THE DRAWINGS

The above and other aspects, features and advantages of certain embodiments of the disclosure will be more apparent from the following detailed description taken in conjunction with the accompanying drawings, in which.

DETAILED DESCRIPTION

Figure 1:
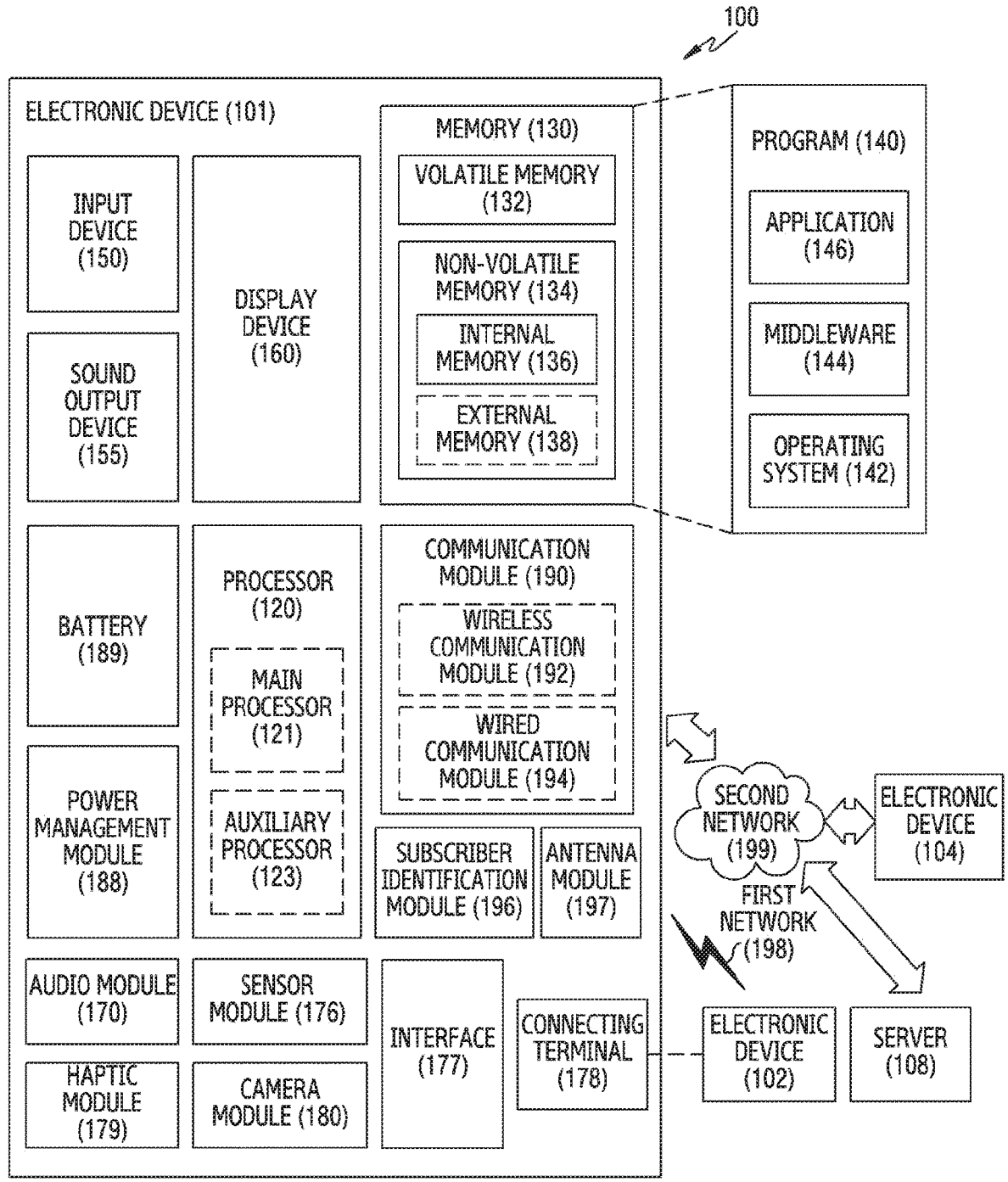
FIG. 1 is a block diagram of an electronic device in a network environment, according to an embodiment.

Embodiments of the disclosure will be described herein below with reference to the accompanying drawings. However, the embodiments of the disclosure are not limited to the specific embodiments and should be construed as including all modifications, changes, equivalent devices and methods, and/or alternative embodiments of the present disclosure. In the description of the drawings, similar reference numerals are used for similar elements.

The terms "have," "may have," "include," and "may include" as used herein indicate the presence of corresponding features (for example, elements such as numerical values, functions, operations, or parts), and do not preclude the presence of additional features.

The terms "A or B," "at least one of A or/and B," or "one or more of A or/and B" as used herein include all possible combinations of items enumerated with them. For example, "A or B," "at least one of A and B," or "at least one of A or B" means (1) including at least one A, (2) including at least one B, or (3) including both at least one A and at least one B.

The terms such as "first" and "second" as used herein may use corresponding components regardless of importance or an order and are used to distinguish a component from another without limiting the components. These terms may be used for the purpose of distinguishing one element from another element. For example, a first user device and a second user device indicates different user devices regardless of the order or importance. For example, a first element may be referred to as a second element without departing from the scope the disclosure, and similarly, a second element may be referred to as a first element.

It will be understood that, when an element (for example, a first element) is "(operatively or communicatively) coupled with/to" or "connected to" another element (for example, a second element), the element may be directly coupled with/to another element, and there may be an intervening element (for example, a third element) between the element and another element. To the contrary, it will be understood that, when an element (for example, a first element) is "directly coupled with/to" or "directly connected to" another element (for example, a second element), there is no intervening element (for example, a third element) between the element and another element.

The expression "configured to (or set to)" as used herein may be used interchangeably with "suitable for," "having the capacity to," "designed to," "adapted to," "made to," or "capable of" according to a context. The term "configured to (set to)" does not necessarily mean "specifically designed to" in a hardware level. Instead, the expression "apparatus configured to . . . " may mean that the apparatus is "capable of . . . " along with other devices or parts in a certain context. For example, "a processor configured to (set to) perform A, B, and C" may mean a dedicated processor (e.g., an embedded processor) for performing a corresponding operation, or a generic-purpose processor (e.g., a central processing unit (CPU) or an application processor (AP)) capable of performing a corresponding operation by executing one or more software programs stored in a memory device.

The terms used in describing the various embodiments of the disclosure are for the purpose of describing particular embodiments and are not intended to limit the disclosure. As used herein, the singular forms are intended to include the plural forms as well, unless the context clearly indicates otherwise. All of the terms used herein including technical or scientific terms have the same meanings as those generally understood by an ordinary skilled person in the related art unless they are defined otherwise. Terms defined in a generally used dictionary should be interpreted as having the same or similar meanings as the contextual meanings of the relevant technology and should not be interpreted as having ideal or exaggerated meanings unless they are clearly defined herein. According to circumstances, even the terms defined in this disclosure should not be interpreted as excluding the embodiments of the disclosure.

The term "module" as used herein may, for example, mean a unit including one of hardware, software, and firmware or a combination of two or more of them. The "module" may be interchangeably used with, for example, the term "unit", "logic", "logical block", "component", or "circuit". The "module" may be a minimum unit of an integrated component element or a part thereof. The "module" may be a minimum unit for performing one or more functions or a part thereof. The "module" may be mechanically or electronically implemented. For example, the "module" according to the disclosure may include at least one of an application-specific integrated circuit (ASIC) chip, a field-programmable gate array (FPGA), and a programmable-logic device for performing operations which has been known or are to be developed hereinafter.

An electronic device according to the disclosure may include at least one of, for example, a smart phone, a tablet personal computer (PC), a mobile phone, a video phone, an electronic book reader (e-book reader), a desktop PC, a laptop PC, a netbook computer, a workstation, a server, a personal digital assistant (PDA), a portable multimedia player (PMP), a MPEG-1 audio layer-3 (MP3) player, a mobile medical device, a camera, and a wearable device. The wearable device may include at least one of an accessory type (e.g., a watch, a ring, a bracelet, an anklet, a necklace, glasses, a contact lens, or a head-mounted device (HMD)), a fabric or clothing integrated type (e.g., an electronic clothing), a body-mounted type (e.g., a skin pad, or tattoo), and a bio-implantable type (e.g., an implantable circuit).

The electronic device may be a home appliance. The home appliance may include at least one of, for example, a television, a digital video disk (DVD) player, an audio, a refrigerator, an air conditioner, a vacuum cleaner, an oven, a microwave oven, a washing machine, an air cleaner, a set-top box, a home automation control panel, a security control panel, a TV box (e.g., Samsung HomeSync™, Apple TV™, or Google TV™), a game console (e.g., Xbox™ and PlayStation™), an electronic dictionary, an electronic key, a camcorder, and an electronic photo frame.

The electronic device may include at least one of various medical devices (e.g., various portable medical measuring devices (a blood glucose monitoring device, a heart rate monitoring device, a blood pressure measuring device, a body temperature measuring device, etc.), a magnetic resonance angiography (MRA), a magnetic resonance imaging (MRI), a computed tomography (CT) machine, and an ultrasonic machine), a navigation device, a global positioning system (GPS) receiver, an event data recorder (EDR), a flight data recorder (FDR), a vehicle infotainment device, an electronic device for a ship (e.g., a navigation device for a ship, and a gyro-compass), avionics, security devices, an automotive head unit, a robot for home or industry, an automatic teller machine (ATM) point of sales (POS) devices, or an Internet of things (IoT) device (e.g., a light bulb, various sensors, electric or gas meter, a sprinkler device, a fire alarm, a thermostat, a streetlamp, a toaster, a sporting goods, a hot water tank, a heater, a boiler, etc.).

The electronic device may include at least one of a part of furniture or a building/structure, an electronic board, an electronic signature receiving device, a projector, and various kinds of measuring instruments (e.g., a water meter, an electric meter, a gas meter, and a radio wave meter). The electronic device may be a combination of one or more of the aforementioned various devices. The electronic device may also be a flexible device. Further, the electronic device is not limited to the aforementioned devices, and may include an electronic device according to the development of new technology.

Hereinafter, an electronic device will be described with reference to the accompanying drawings. In the disclosure, the term "user" indicates a person using an electronic device or a device (e.g., an artificial intelligence electronic device) using an electronic device.

FIG. 1 is a block diagram of an electronic device in a network environment, according to an embodiment. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a CPU or an AP), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an ISP or a CP) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by another component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming call. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wired) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wired) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, ISPs, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more CPs that are operable independently from the processor 120 (e.g., the AP) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., a printed circuit board (PCB)). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2:
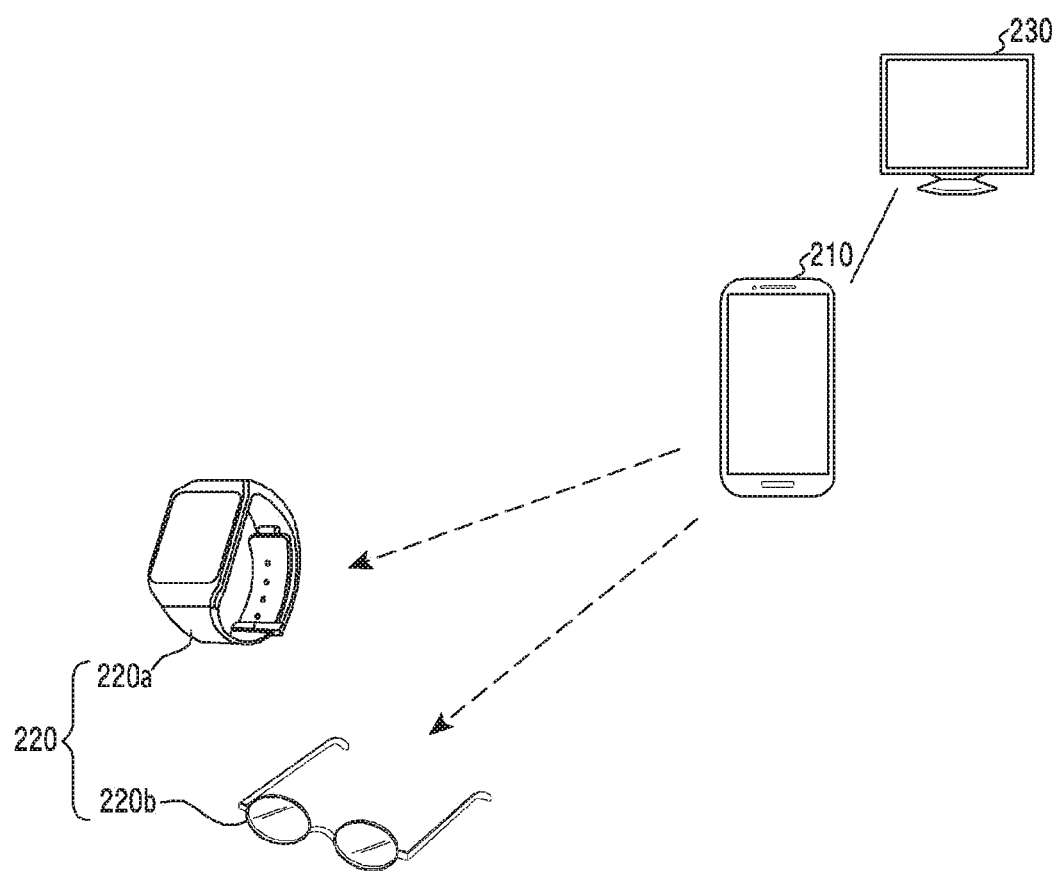
FIG. 2 is a diagram of electronic devices for providing a stress management service, according to an embodiment.

FIG. 2 is a diagram of electronic devices for providing a stress management service, according to an embodiment.

Referring to FIG. 2, one embodiment may include a first electronic device 210 (e.g., an electronic device 101), a second electronic device 220, and/or a third electronic device 230.

The first electronic device 210 may be a portable electronic device such as a smartphone or a tablet PC. The first electronic device 210 may operate alone or may operate by being functionally connected to the second electronic device 220 and/or the third electronic device 230.

The first electronic device 210 may obtain biometric information of a user. The first electronic device 210 may extract a bio-signal (e.g., a heart rate), based on a facial image of the user photographed through a camera module (e.g., a camera module 180). The first electronic device 210 may photograph the face of the user for a predetermined time (e.g., 10 seconds) or more through a camera, and extract a photoplethysmogram (PPG) signal from skin color data.

The first electronic device 210 may measure heart rate variability by using a camera (not shown) and a flash (not shown). When a user covers the camera and the flash with his/her finger (e.g., an index finger), light from the flash is incident on the camera through the finger, and the first electronic device 210 may measure a heart rate by analyzing a change in the light incident on the camera. The measurement is based on the principle that the amount of the light incident on the camera changes as blood flow changes in the finger according to heartbeat.

The first electronic device 210 may measure a heart rate, heart rate variability, and/or a blood pressure through a separate biometric sensor (e.g., a heart rate measurement sensor). The heart rate measurement sensor may measure a heart rate by using infrared light.

The first electronic device 210 may obtain heart rate, heart rate variability, and/or blood pressure information of a user through a sensor module (e.g., a sensor module 176).

The first electronic device 210 may receive and obtain biometric information (e.g., heart rate, heart rate variability, and/or blood pressure information) of a user from the second electronic device 220.

The first electronic device 210 may calculate a stress value of a user, based on biometric information obtained from at least one of the first electronic device 210 or the second electronic device 220.

The first electronic device 210 may determine whether stress occurs, based on the calculated stress value. When the stress value satisfies a designated condition, the first electronic device 210 may determine that stress has occurred. The first electronic device 210 may determine whether stress occurs by continuously or periodically obtaining biometric information of a user.

When it is determined that stress of a user occurs or that stress can occur, the first electronic device 210 may provide information for stress relief (hereinafter, referred to as a stress relief method). The stress relief method may include at least one of an action for stress relief (e.g., a breathing therapy or a meditation therapy), content (e.g., a music or a movie), and a place (e.g., a house or an arboretum). The stress relief method may be provided through at least one of the first electronic device 210, the second electronic device 220, or the third electronic device 230. The detailed description thereof will be described later with reference to FIGS. 7A to 7H.

The first electronic device 210 may provide a stress relief method appropriate for contextual information (e.g., a time, a place, and an occasion) in consideration of current contextual information of a user. The first electronic device 210 may recommend a breathing therapy or a meditation therapy when the user is in a sedentary state where the user hardly moves. Alternatively, the first electronic device 210 may recommend music when the user is moving. Alternatively, the first electronic device 210 may provide a nearby recommendation place (e.g., an arboretum, a flower shop, or a restaurant), based on location information of the user. The detailed description thereof will be described later with reference to FIG. 6.

The first electronic device 210 may provide a personalized stress relief method. After a user performs a stress relief method, the first electronic device 210 may give a weight to the stress relief method, based on information on stress change of the user. When a stress value is lowered by a stress relief method, the first electronic device 210 may provide a larger weight to the stress relief method. On the contrary, when a stress value of a user is maintained or increases by a stress relief method, the first electronic device 210 may lower the weight given to the stress relief method. When it is determined that a stress relief method does not help to relieve stress of a user (e.g., when a weight is reduced to less than a designated value), the first electronic device 210 may remove the corresponding stress relief method. The detailed description thereof will be described later with reference to FIG. 4B.

The first electronic device 210 may manage (e.g., store) a stress history of a user. The first electronic device 210 may periodically or continuously measure a stress value, and collect and store contextual information at the time of stress occurrence. When stress occurrence is detected, the first electronic device 210 may collect the contextual information through at least one of the first electronic device 210, the second electronic device 220, and/or the third electronic device 230. The contextual information may include first contextual information collected through a sensor and second contextual information collected through a log record of the first electronic device 210. The first contextual information may include location information of the first electronic device 210 obtained through GPS and Wi-Fi, and user's movement or exercise state information obtained through a motion sensor. The second contextual information may include content reproduced at the time of or just before stress occurrence, an executed application, and weather (e.g., a temperature, humidity, ultraviolet light, atmospheric pressure, etc.).

The first electronic device 210 may store a stress history by mapping stress occurrence information and contextual information at the time of stress occurrence. The first electronic device 210 may estimate (predict) stress occurrence of a user, based on the stress occurrence history and the contextual information. When the first electronic device 210 obtains the contextual information mapped to the stress occurrence history of the user, the first electronic device 210 may estimate that the user is stressed or is highly likely to be stressed. If stress is high near the user's company every Monday morning at 9 A.M., the first electronic device 210 may provide an alarm for stress occurrence (e.g. a message like "Stress is expected to come your way in one hour. Get ready.") before 9 A.M. (e.g. 8 A.M.) on Monday morning, or may provide a consolation message (e.g., a message like "Are you all right?") later (e.g., 10 A.M.).

The second electronic device 220 may be a wearable electronic device such as a smart watch 220a or smart glasses 220b. The second electronic device 220 may be a skin-attachable electronic device such as a skin pad, a bio-implantable electronic device, or a smart medical device.

The wearable electronic device of the second electronic device 220 may include a biometric sensor (e.g., a heart rate measurement sensor) at a portion (e.g., the bottom surface) which comes into contact with the user's skin, and a body-attachable electronic device may be attached to a body part (e.g., an arm, a wrist, a leg, a neck, a head, etc.) to measure heart rate variability.

The second electronic device 220 may be connected by wire or wirelessly to an external electronic device (e.g., the first electronic device 210 or a server) to transmit a measurement result to the external electronic device.

Similar to the first electronic device 210, the second electronic device 220 may obtain biometric information to measure stress. The second electronic device 220 may obtain biometric information such as a heart rate, heart rate variability, or a blood pressure, based on a bio-signal (e.g., a PPG or an electrocardiogram (ECG)) obtained through a sensor, and measure stress, based on the biometric information. The second electronic device 220 may continuously or periodically measure and store stress. When a stress value satisfies a designated condition, the second electronic device 220 may guide (provide) a stress relief method to a user. The second electronic device 220 may provide a stress relief method, based on current contextual information of the user. The second electronic device 220 may measure the degree of stress reduction according to each stress relief method and apply a measurement result to provide a personalized stress relief method. The second electronic device 220 may provide an alarm by predicting a stressful occasion, based on a stress history.

The second electronic device 220 may operate alone or may operate by being functionally connected to the first electronic device 210 and/or the third electronic device 230. The second electronic device 220 may transmit measured biometric information to the first electronic device 210 and receive a stress relief method from the first electronic device 210 to provide the stress relief method (e.g., display the stress relief method on a display).

When stress occurs, the second electronic device 220 may provide a stress relief method through the first electronic device 210 or the third electronic device 230.

The second electronic device 220 may receive contextual information at the time of stress occurrence from the first electronic device 210 or the third electronic device 230. When the second electronic device 220 does not include a location measurement module (e.g., a GPS), the second electronic device 220 may receive location information from the first electronic device 210. Alternatively, when stress occurrence is detected, the second electronic device 220 may request and receive information on content being reproduced or information on an application being executed from the first electronic device 210 or the third electronic device 230.

The second electronic device 220 may receive a measured stress value from the first electronic device 210, and compare or combine the received stress value with a stress value measured by itself to determine a stress value.

The second electronic device 220 may periodically receive contextual information from the first electronic device 210 and/or the third electronic device 230, and predict a stress occurrence occasion.

The third electronic device 230 is an external device which can be connected by wire or wirelessly to the first electronic device 210 or the second electronic device 220, and may include a television, a monitor, etc. having a relatively large screen. The third electronic device 230 may be an IoT device such as a light or an air purifier. The third electronic device 230 may include a vehicle.

The third electronic device 230 may provide a stress relief method received from the first electronic device 210 and/or the second electronic device 220 connected by wire or wirelessly thereto. The third electronic device 230 may receive and output content such as a meditation image or a yoga image. The third electronic device 230 may receive a link for providing content (e.g., meditation, breathing, and yoga images) from the first electronic device 210 or the second electronic device 220, and access the link to output the content.

When the third electronic device 230 receives a request for transmission of contextual information from the first electronic device 210 and/or the second electronic device 220, the third electronic device 230 may provide the contextual information (e.g., information on a program being viewed, air condition, traffic condition, etc.) to the first electronic device 210 and/or the second electronic device 220.

Figure 3:
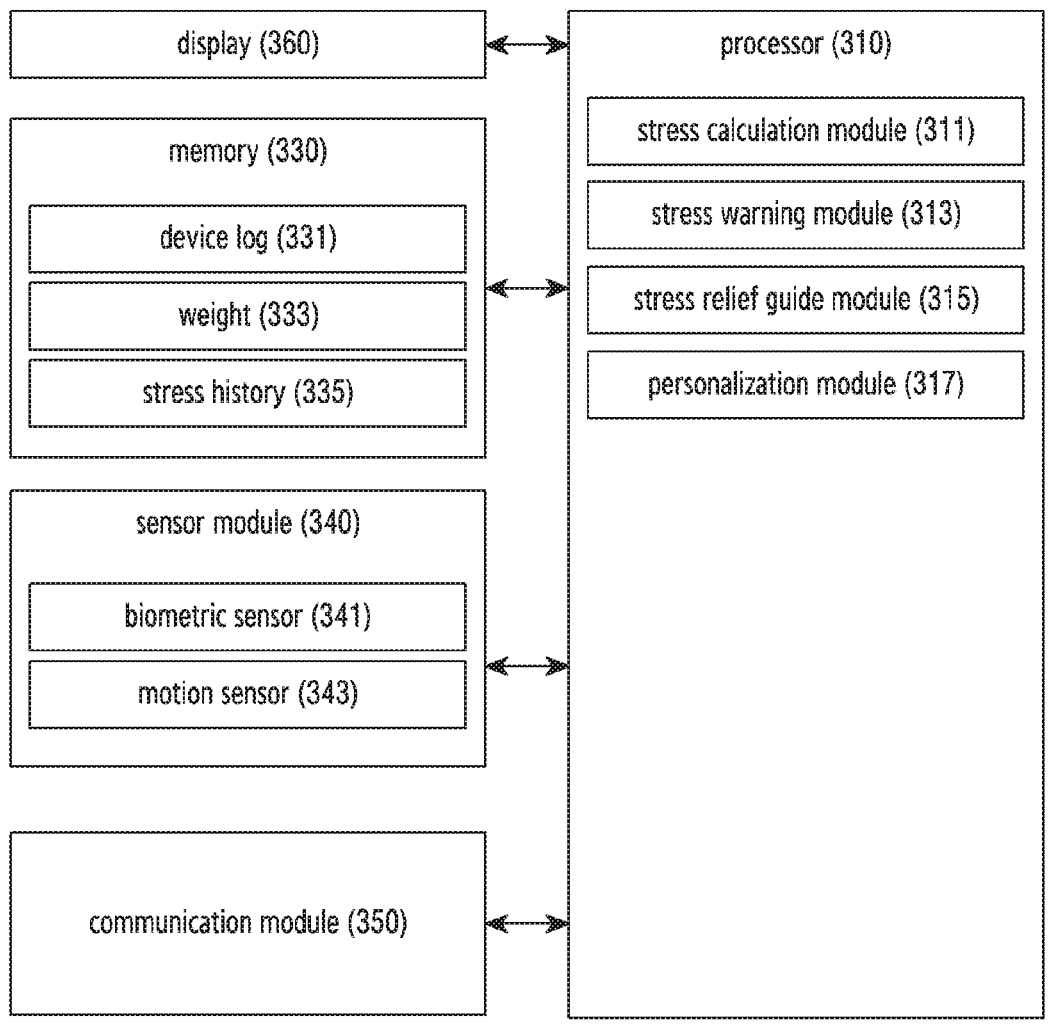
FIG. 3 is a diagram of a configuration of an electronic device, according to an embodiment.

FIG. 3 is a diagram of a configuration of an electronic device, according to an embodiment.

An electronic device 300 of FIG. 3 may be the first electronic device 210 or the second electronic device 220 of FIG. 2.

Referring to FIG. 3, the electronic device 300 may include a processor 310, a memory 330, a sensor module 340, a communication module 350, and a display 360.

The processor 310 may control the overall operation of the electronic device 300.

The processor 310 may control each component of the electronic device 300. The processor 300 may receive a command or instructions from the memory 330 and control each component according to the received command or instructions to perform various functions.

The processor 310 may include a stress calculation module 311, a stress warning module 313, a stress relief guide module 315, and a personalization module 317.

The stress calculation module 311 may calculate (compute) a stress value, based on heart rate variability measured by a biometric sensor 341. The stress calculation module 311 may calculate a stress value by using various known algorithms (e.g., pNNx (the proportion derived by dividing the number of interval differences of successive R-R interval greater than x msec by the total number of R-R interval), pNN40-Median, pNN10-Median, SDNN (standard deviation of the node to node intervals)-Median, and RMSSD (Root mean square of successive difference)-Median).

The stress warning module 313 may warn about an occasion where stress may occur, based on a stress history 335. The stress warning module 313 may provide an alarm at the time of detection of a specific place, time, and/or occasion when there is a stress occurrence history of a user at the specific place, time, and/or occasion. Alternatively, the stress warning module 313 may periodically obtain contextual information and provide an alarm when there is a stress history having contextual information corresponding to the obtained contextual information. When stress is high at a specific time (e.g., 30 minutes before bedtime), the stress warning module 313 may warn of difficulty in a deep sleep due to stress.

The stress relief guide module 315 may guide various stress relief methods for stress relief at the time of detection of stress occurrence. The stress relief guide module 315 may obtain user's contextual information (a location, a time, a movement, and an exercise state), and provide at least one stress relief method appropriate for the obtained contextual information among the various stress relief methods. The stress relief guide module 315 may first provide a relief method having the highest priority (e.g., a weight) or may allow the relief method of the highest priority to be located at the top of a list.

The stress relief guide module 315 may guide a stress relief method to enable a user to have a deep sleep when stress is high at a specific time (e.g., 30 minutes before bedtime).

The personalization module 317 may control weights for various stress relief methods. The personalization module 317 may give a weight to each stress relief method, based on the degree of stress reduction. The personalization module 317 may give a larger weight to a method showing a larger degree of stress reduction, so that the method can be preferentially provided.

The memory 330 may be disposed inside a housing of the electronic device 300 and operatively (or functionally) connected to the processor 310. The memory 330 may store various programs and store data downloaded or data generated while performing the various programs. The memory 330 may store various commands and/or instructions for operating the processor 310. The memory 330 may include at least one of an internal memory or an external memory.

The memory 330 may store a program which allows the processor 310 to perform various operations related to measurement, detection, warning, and/or relief of stress. The memory 330 may store a device log 331 including a playing history of content, an execution history of an application, and the like, a weight 333 for each stress relief method, and the stress history 335 measured for a predetermined period of time.

The display 360 may be exposed through a first surface (front surface) of the housing of the electronic device 300, and may provide an output function. The display 360 may display a stress measurement result and/or a stress relief method. The display 360 may display a stress relief method in various forms as shown in FIGS. 7A to 7F.

The sensor module 340 may include the biometric sensor 341 and a motion sensor 343.

The biometric sensor 341 may measure biometric information (e.g., a heart rate, heart rate variability, a blood pressure, etc.) of a user according to a user's request or a configured period. The biometric sensor 341 may include an ECG sensor or a PPG sensor.

The motion sensor 343 may measure a movement and/or a posture of a user.

The motion sensor 343 may measure whether the user is moving, stationary, lying, standing, repeating similar actions, walking, and/or running.

The communication module 350 may be disposed inside the housing of the electronic device 300 and may perform wired communication and/or wireless communication. The communication module 350 may connect a communication channel with an external electronic device. The communication module 350 may transmit a stress relief method to an external electronic device (e.g., the third electronic device 230) under the control of the processor 310. The communication module 350 may receive contextual information from at least one external electronic device (e.g., the second electronic device 220).

The communication module 350 may continuously or periodically transmit measured stress and contextual information at the time of stress occurrence to an external electronic device (e.g., a stress history management server) under the control of the processor 310.

In addition, the communication module 350 may transmit the contextual information at the time of stress occurrence to the stress history management server under the control of the processor 310, and receive a stress relief method appropriate for the contextual information and/or a user of the electronic device 300 from the stress history management server.

Figure 4A:
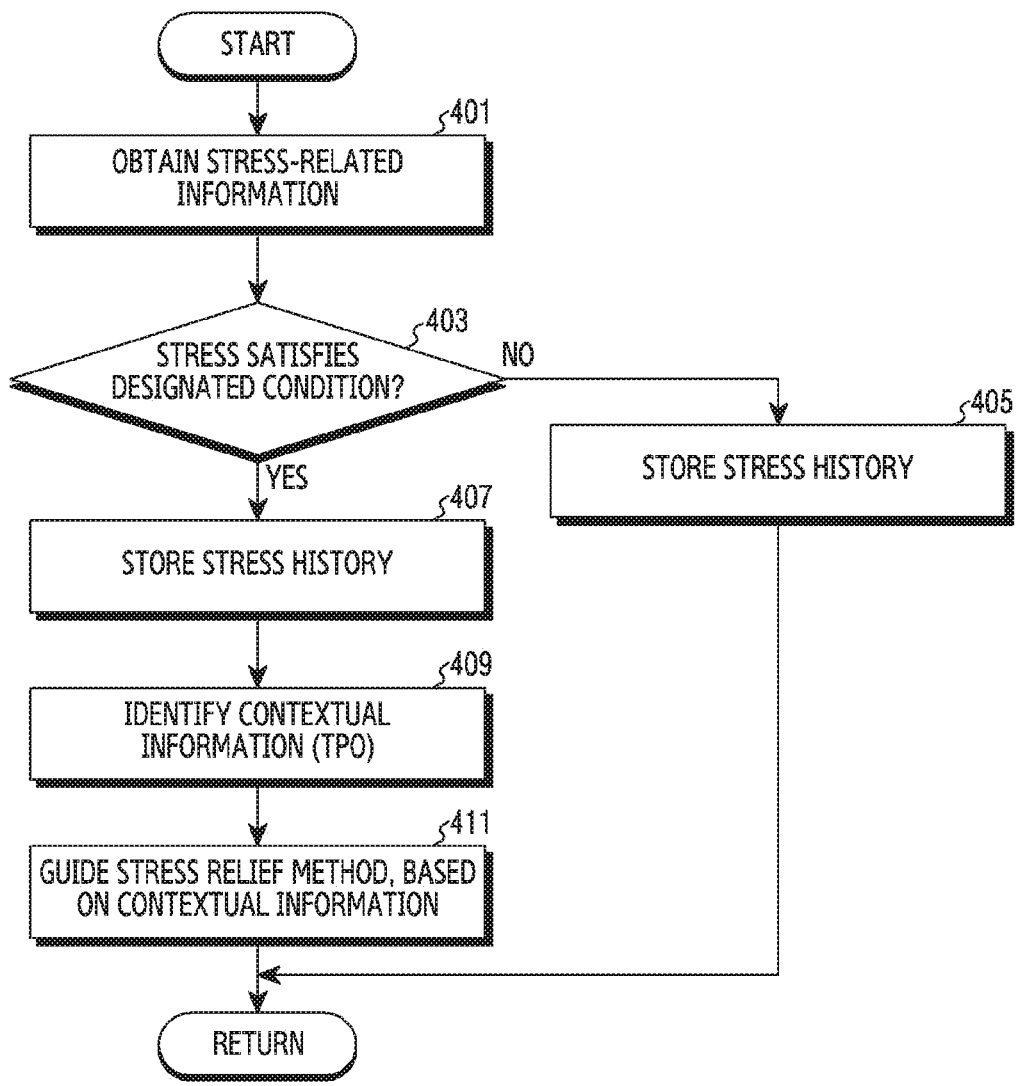
FIG. 4A is a flowchart of a method for providing information for stress relief by an electronic device, according to an embodiment.

FIG. 4A is a flowchart of a method for providing information for stress relief by an electronic device, according to an embodiment.

Referring to FIG. 4A, at step 401, a processor (e.g., the processor 120 or the processor 310) of an electronic device (e.g., the electronic device 101, the first electronic device 210, the second electronic device 220, or the electronic device 300) may obtain stress-related information (e.g., a stress value). The processor may obtain biometric information (e.g., a heart rate, heart rate variability, and a blood pressure) through a biometric sensor (e.g., a PPG sensor, an ECG sensor, or a heart rate sensor), and may calculate a stress value, based on the obtained biometric information.

At step 403, the processor may determine whether stress satisfies a designated condition. The processor may determine whether a stress value exceeding a first threshold (e.g., level 75 in the case of stress values classified into 100 levels) persists beyond a second threshold (e.g., 5 minutes or 300 times). Step 403 will be described in detail later with reference to FIG. 5.

As a result of the determination of step 403, when the stress does not satisfy the designated condition, the processor may store a stress history at step 405. The processor may obtain contextual information at the time of stress occurrence, and map and store the stress value and the contextual information. The contextual information may include location information collected through a sensor included in the electronic device, a user's movement information or exercise state information, currently reproduced content collected through a log record, an executed application, weather, and the like. The contextual information may be received from external electronic devices (e.g., IoT devices) connected through communication.

As a result of the determination of step 403, when the stress satisfies the designated condition, the processor may store a stress history at step 407. Since step 407 is the same as or similar to operation 405, the detailed description thereof will be omitted.

At step 409, the processor may identify contextual information (e.g., a time, a place, and/or an occasion).

At step 411, the processor may guide (provide) a stress relief method, based on the contextual information. The processor may visually (e.g., via a display) or auditorily (e.g., via a speaker) guide a stress relief method through a user interface. The detailed description of the collection of the contextual information and the guide of the stress relief method will be described later with reference to FIG. 6.

Figure 4B:
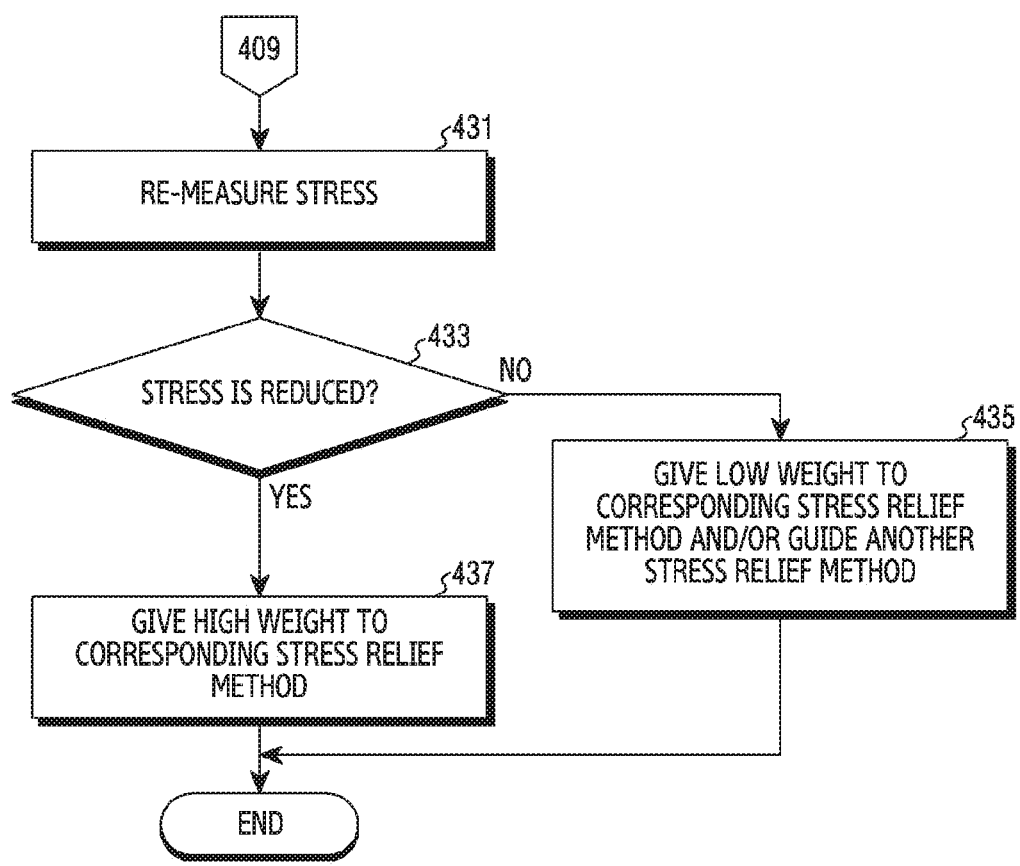
FIG. 4B is a flowchart of a method for providing information for stress relief by an electronic device, according to an embodiment.

FIG. 4B is a flowchart of a method for providing information for stress relief by an electronic device, according to an embodiment.

FIG. 4B describes operations after operations 401 to 409 of FIG. 4A are performed.

Referring to FIG. 4B, at step 431, a processor of an electronic device may re-measure stress. The processor may guide a stress relief method and then re-measure stress after a predetermined period of time has elapsed. The processor may determine whether the stress relief method is implemented, and re-measure stress when the implementation of the stress relief method is identified. When "listening to music" has been guided as a stress relief method, the processor may re-measure stress while or after a corresponding piece of music is played through the electronic device or an external device connected to the electronic device.

At step 433, the processor may determine whether stress has been reduced as a result of the re-measurement. As a result of the determination of step 433, when the stress is not reduced, the processor may give a low weight to the corresponding stress relief method and/or guide another stress relief method at step 435. The processor may exclude the stress relief method such that the stress relief method is not guided to a user in a corresponding occasion.

As a result of the determination of step 433, when the stress is reduced, at step 437, the processor may give a high weight to the corresponding stress relief method.

Figure 5:
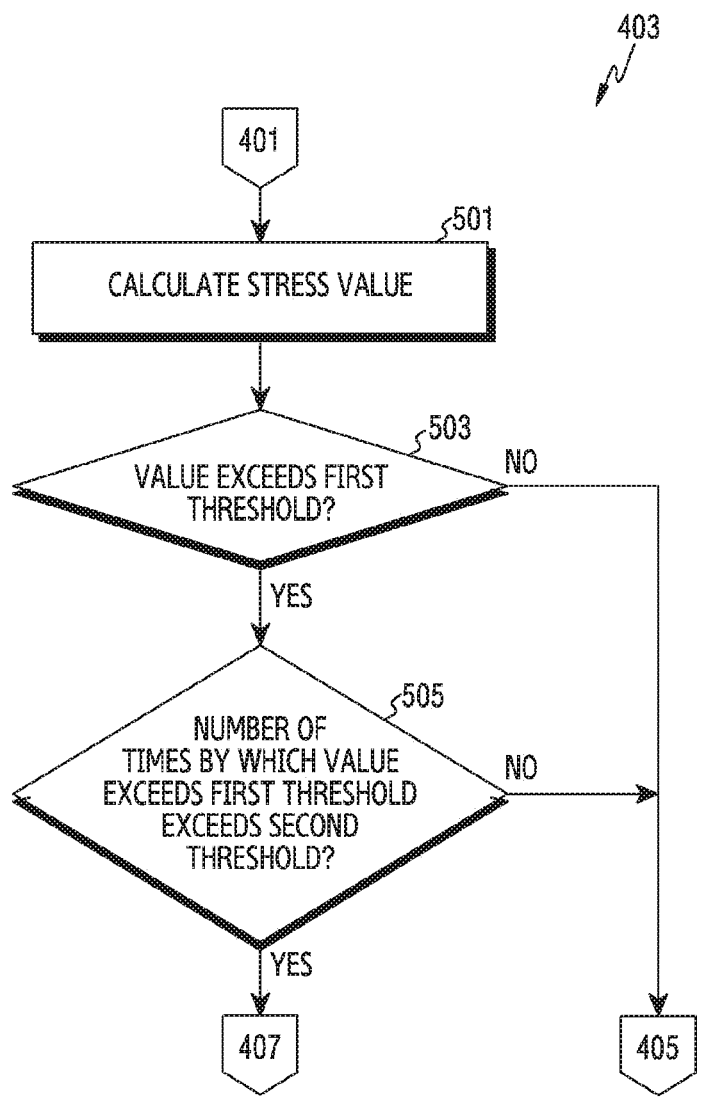
FIG. 5 is a flowchart of a method for determining whether stress occurs by an electronic device, according to an embodiment.

FIG. 5 is a flowchart of a method for determining whether stress occurs by an electronic device, according to an embodiment.

Referring to FIG. 5, at step 501, a processor of an electronic device may calculate a stress value. The processor (e.g., the stress calculation module 311) may calculate (or compute) the stress value through various known algorithms, based on biometric information.

At step 503, the processor may determine whether the stress value exceeds (or is greater than or equal to) a first threshold. The first threshold may be level 75 in the case of dividing stress levels divided from 1 to 100.

As a result of the determination of step 503, when the stress value does not exceed the first threshold, the processor may return to step 405 of FIG. 4A. On the other hand, as a result of the determination of step 503, when the stress value exceeds the first threshold, at step 505, the processor may determine whether the number of times by which the stress value exceeds the first threshold exceeds (or is greater than or equal to) a second threshold (e.g., 300 times). The processor may determine whether a maintaining time of stress exceeding the first threshold is maintained beyond (or more than or equal to) a third threshold (e.g., 5 minutes).

As a result of the determination of step 505, when the number of times by which the stress value exceeds the first threshold does not exceed the second threshold, the processor may proceed to step 405 of FIG. 4A. On the other hand, as a result of the determination of step 505, when the number of times by which the stress value exceeds the first threshold exceeds the second threshold, the processor may proceed to step 407 of FIG. 4A. As such, when a stress of level 75 or higher occurs 300 times or more, or is maintained for 5 minutes or more, the processor of the electronic device may determine that stress satisfies a designated condition (that user's stress is high).

There may be a plurality of first thresholds, and the processor may variously provide (guide) stress-related information, based on each of the plurality of first thresholds. The processor may provide a warning message (e.g., a pop-up message, a sound effect output, an output of vibration having a specified pattern, etc.) notifying that stress occurrence is expected when stress exceeding a (1-1)th threshold (e.g., 60) persists beyond the second threshold, may provide a notification message to notify a user of stress occurrence when stress exceeding a (1-2)th threshold (e.g., 70) persists beyond the second threshold, and may provide a stress relief method when stress exceeding a (1-3)th threshold (e.g., 75) persists beyond the second threshold. This is merely an example and does not limit the embodiment.

Figure 6:
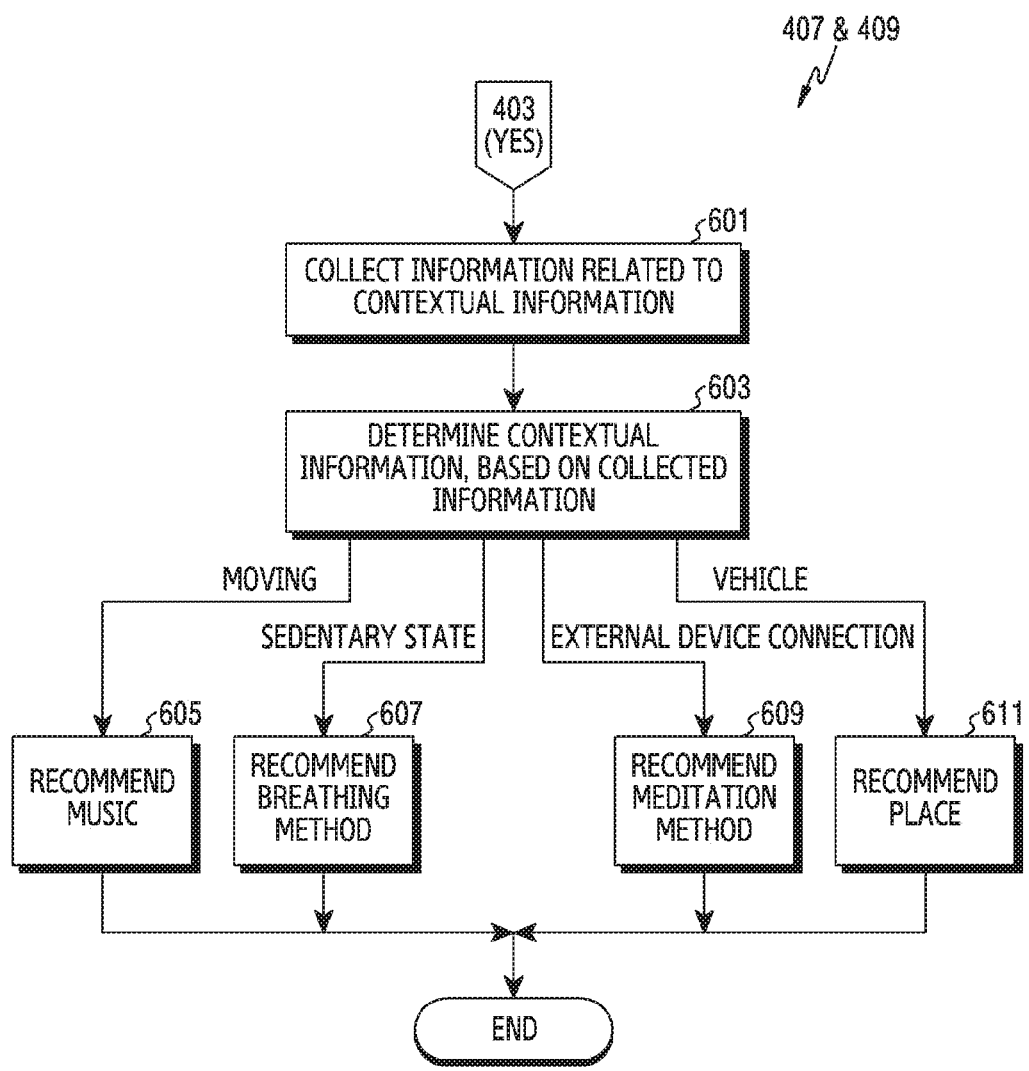
FIG. 6 is a flowchart of a method for providing a stress relief method, according to an embodiment.

FIG. 6 is a flowchart of a method for providing a stress relief method, according to an embodiment.

Referring to FIG. 6, at step 601, a processor of an electronic device may collect information related to contextual information. The processor may collect a current location (place), a current time, an occasion (content or an application being executed, and weather), and user's movement or exercise state information.

At step 603, the processor may determine the contextual information, based on the collected information. The processor may determine whether a user is moving, the user is in a sitting posture, an external device is connected, or the user rides in a vehicle.

At steps 605 to 611, the processor may guide a stress relief method, based on the determined contextual information. As at step 605, the processor may recommend music (e.g., Bach's music or K-pop) when the user is moving. Alternatively, as at step 607, the processor may recommend a breathing method when the user is in a sedentary state. As at step 609, the processor may recommend a meditation method when there is an external device (e.g., a television) connected to the electronic device. As at step 611, the processor may recommend a place (e.g., an arboretum, a flower shop, or a book store) when the electronic device is connected to a vehicle (the user rides in a vehicle). The processor may determine a recommendation place by reflecting user's preference based on big data. The processor may search for content (e.g., a meditation image, a breathing image, etc.) corresponding to the determined stress relief method from an external server, and provide a link to the corresponding content.

Meanwhile, steps 605 to 611 are merely examples and do not limit various embodiments. Contextual information and stress relief methods may be various.

FIGS. 7A-7H are diagrams of examples of providing information for stress relief by an electronic device, according to an embodiment.

Referring to FIGS. 7A to 7H, an electronic device may provide information for stress relief when it is determined that stress has occurred. When it is determined that stress has occurred, the electronic device may provide a screen for suggesting a breathing exercise (hereinafter, referred to as a breathing screen), as shown in reference numeral 710 of FIG. 7A. The breathing screen may include a control bar 701a which can play recommended music in one region. The control bar 701a may be displayed on the screen in a floating manner to be movable. Accordingly, when the breathing exercise is possible, a user may relieve stress by performing the breathing exercise or performing the breathing exercise and listening to music together. Alternatively, when the breathing exercise is impossible, the user may relieve stress by listening to music. When a starting menu 701b is selected (e.g., touched), the electronic device may output a breathing guide screen as shown in the drawing of reference numeral 720. The breathing guide screen may guide an inhalation time and an exhalation time.

Figure 7A:
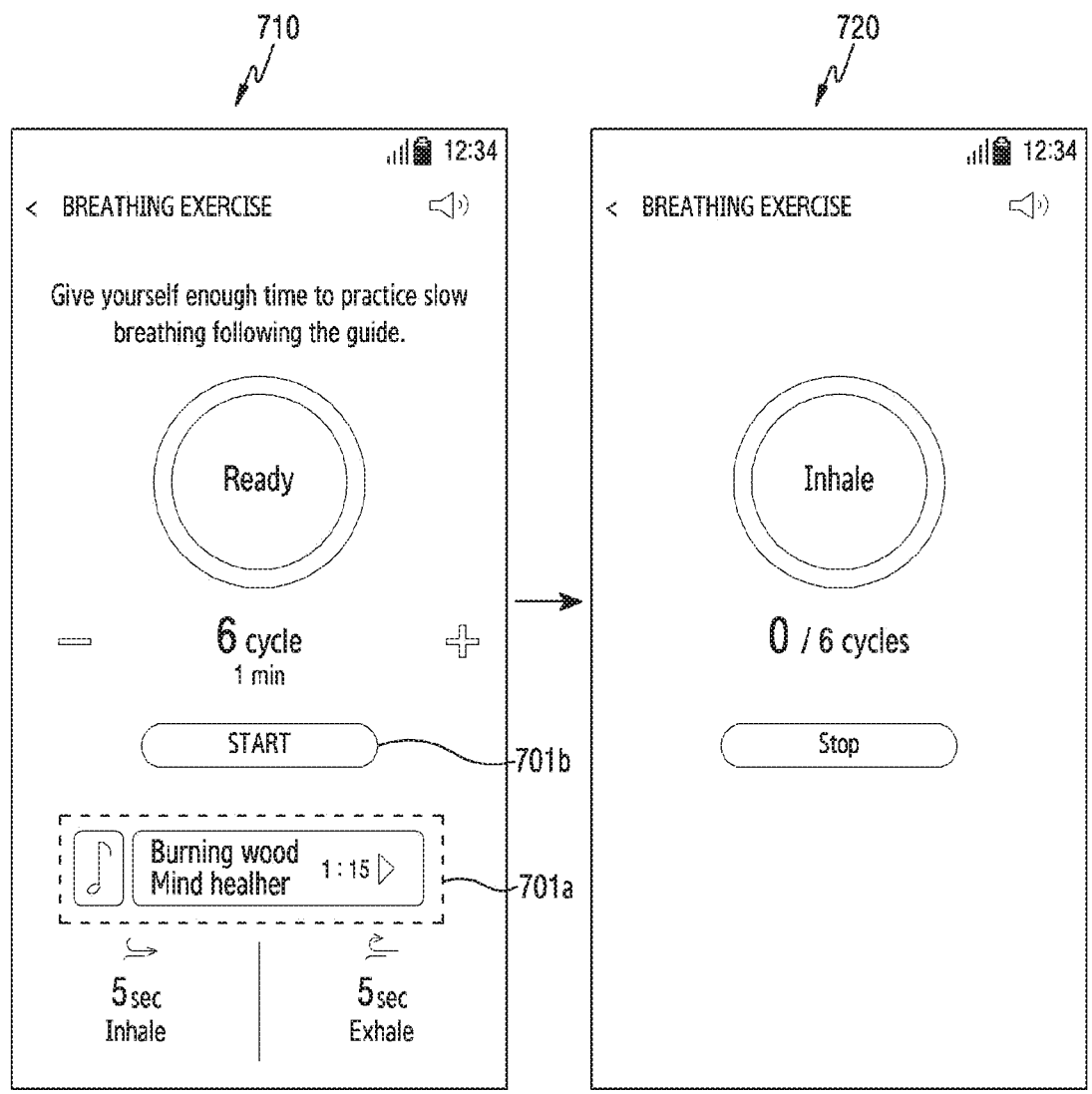
FIG. 7A is a diagram of an example of providing information for stress relief by an electronic device, according to an embodiment.
Figure 7B:
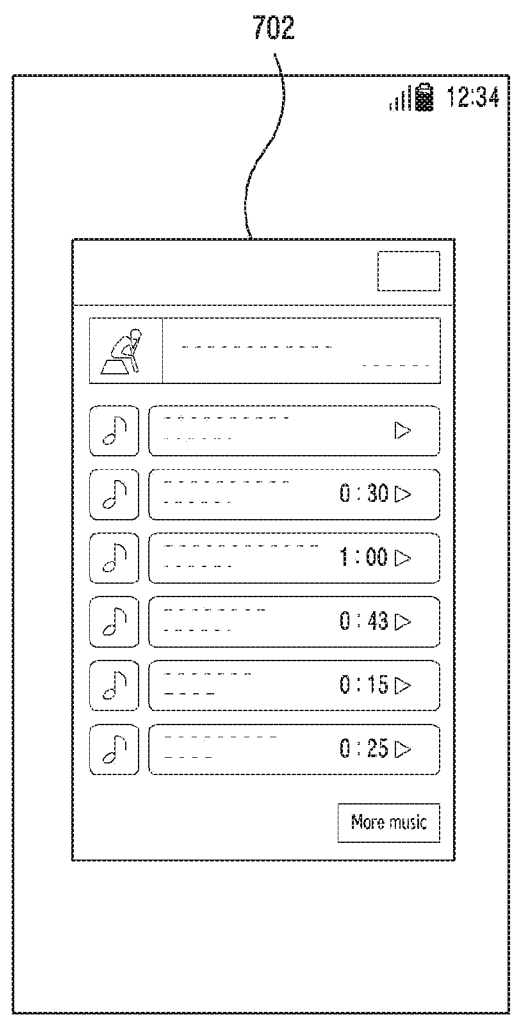
FIG. 7B is a diagram of an example of providing information for stress relief by an electronic device, according to an embodiment.

When it is determined that stress has occurred, the electronic device may provide a recommended music list 702 on a screen as shown in FIG. 7B. The recommended music list 702 may include pieces of music arranged in a sequence in which a piece showing a larger degree of stress reduction precedes a piece showing a smaller degree thereof. The recommended music list 702 may be changed according to users since the list reflects personalization.

Figure 7C:
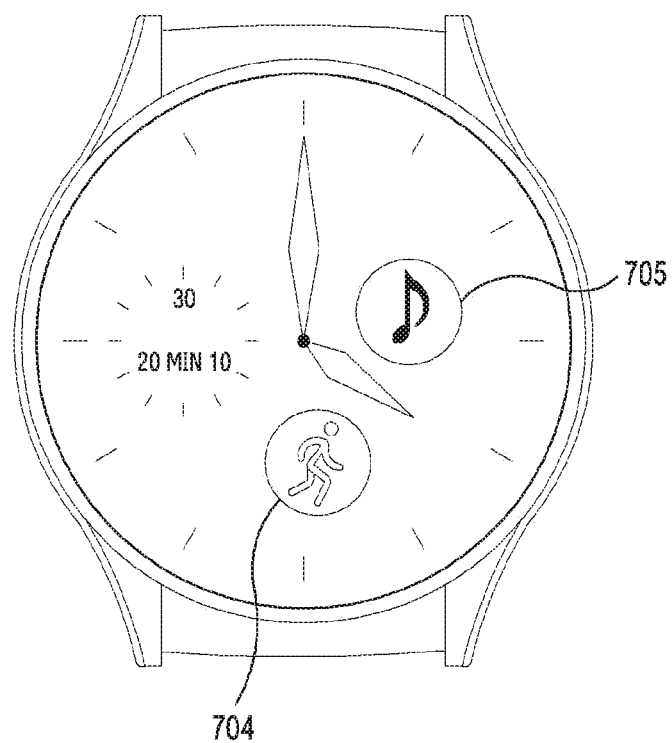
FIG. 7C is a diagram of an example of providing information for stress relief by an electronic device, according to an embodiment.

When it is determined that stress has occurred, as shown in FIG. 7C, the electronic device may provide, on a screen, a first visual indicator 704 for inducing exercise and a second visual indicator 705 for inducing listening to music.

Figure 7D:
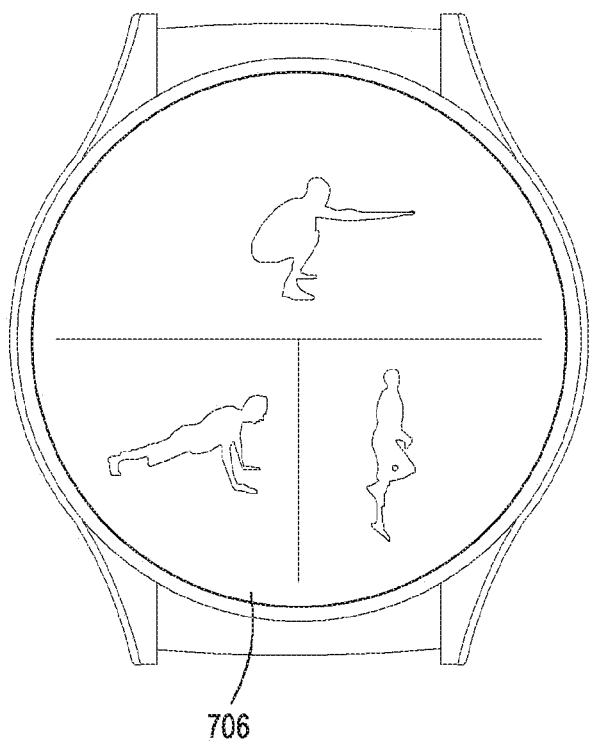
FIG. 7D is a diagram of an example of providing information for stress relief by an electronic device, according to an embodiment.

When the first visual indicator 704 is selected (e.g., touched), the electronic device may display a recommended exercise list 706 on the screen as shown in FIG. 7D. In this case, the electronic device may display an exercise having a high weight on the top. When a specific exercise is selected in the recommended exercise list 706, the electronic device may display, on the screen, an image for guiding the selected exercise method.

Figure 7E:
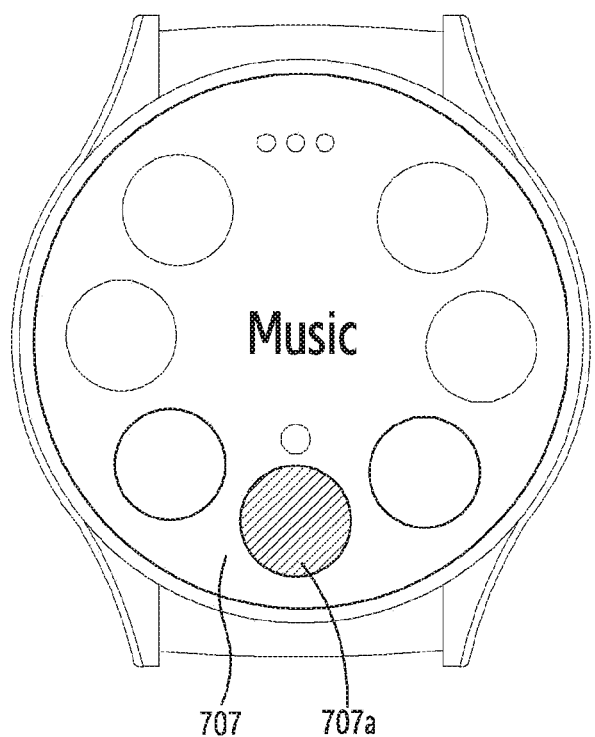
FIG. 7E is a diagram of an example of providing information for stress relief by an electronic device, according to an embodiment.
Figure 7F:
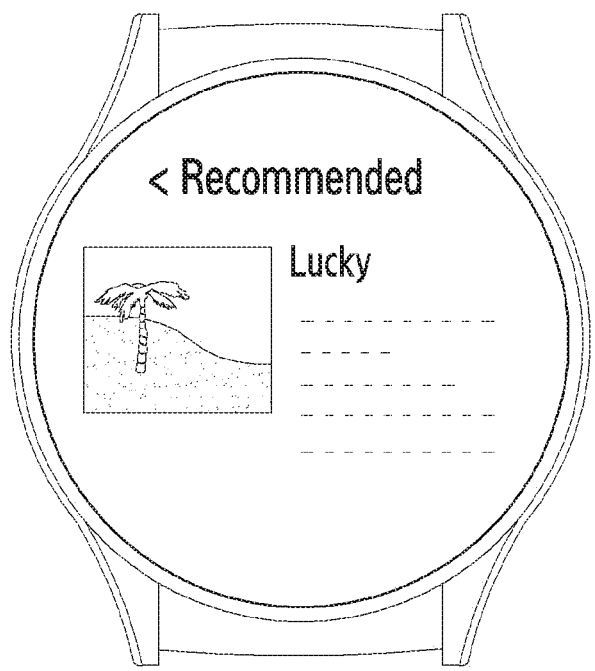
FIG. 7F is a diagram of an example of providing information for stress relief by an electronic device, according to an embodiment.

When the second visual indicator 705 is selected (e.g., touched), the electronic device may display a recommended music list 707 on the screen as shown in FIG. 7E. In this case, the electronic device may display a relatively large icon of music having a high weight. When a specific music 707a is selected in the recommended music list 707, the electronic device may display a playback screen of the selected specific music 707a as shown in FIG. 7F.

Figure 7G:
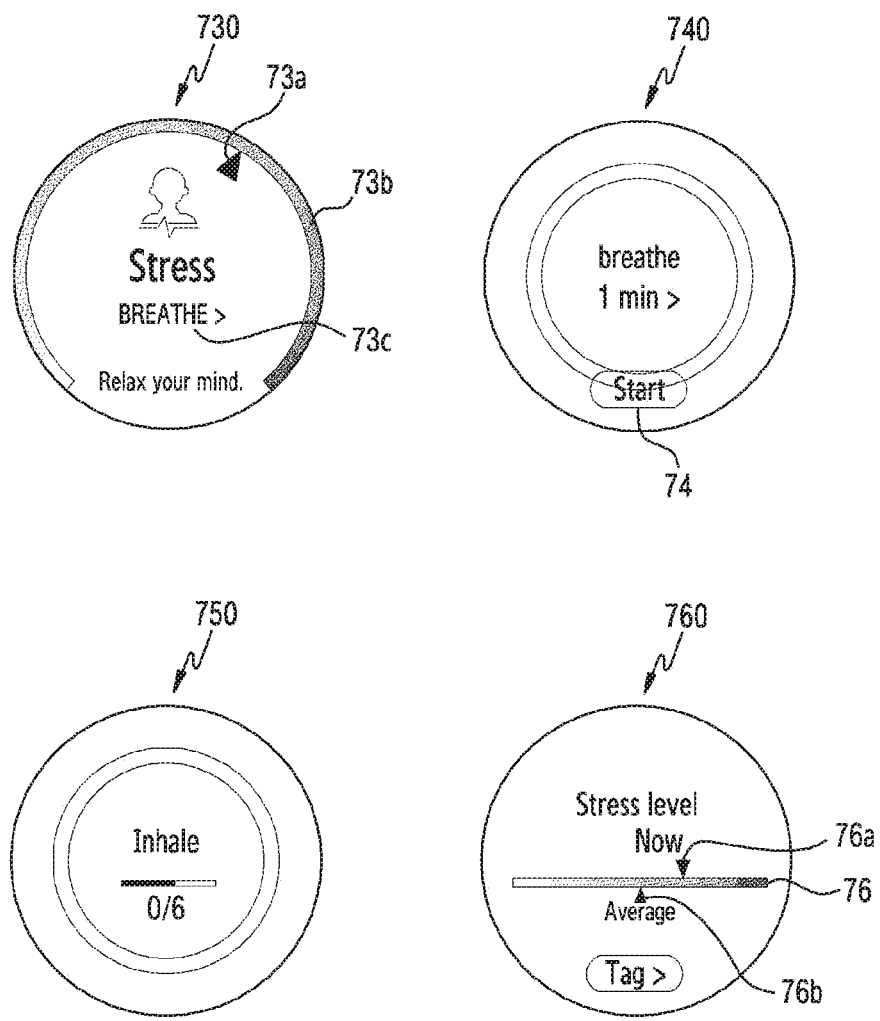
FIG. 7G is a diagram of an example of providing information for stress relief by an electronic device, according to an embodiment.

When it is determined that stress has occurred, the electronic device may output a breathing recommendation screen on a display as shown in the drawing of reference numeral 730 of FIG. 7G. The breathing recommendation screen may include a circular graph 73b indicating a measured stress measurement result 73a and recommendation information 73c. The drawing of reference numeral 730 shows an example of recommending a breathing exercise. When the recommendation information 73c is selected, the electronic device may output a breathing preparation screen on the display as shown in the drawing of reference numeral

740. When a starting menu 74 is selected, the electronic device may output a breathing guide screen on the display as shown in the drawing of reference numeral 750. When the breathing exercise is completed, the electronic device may output a breathing completion screen on the display as shown in the drawing of the reference numeral 760. The breathing completion screen may include a bar graph 76 indicating a stress level 76a measured during the breathing exercise and an average stress level 76b.

Figure 7H:
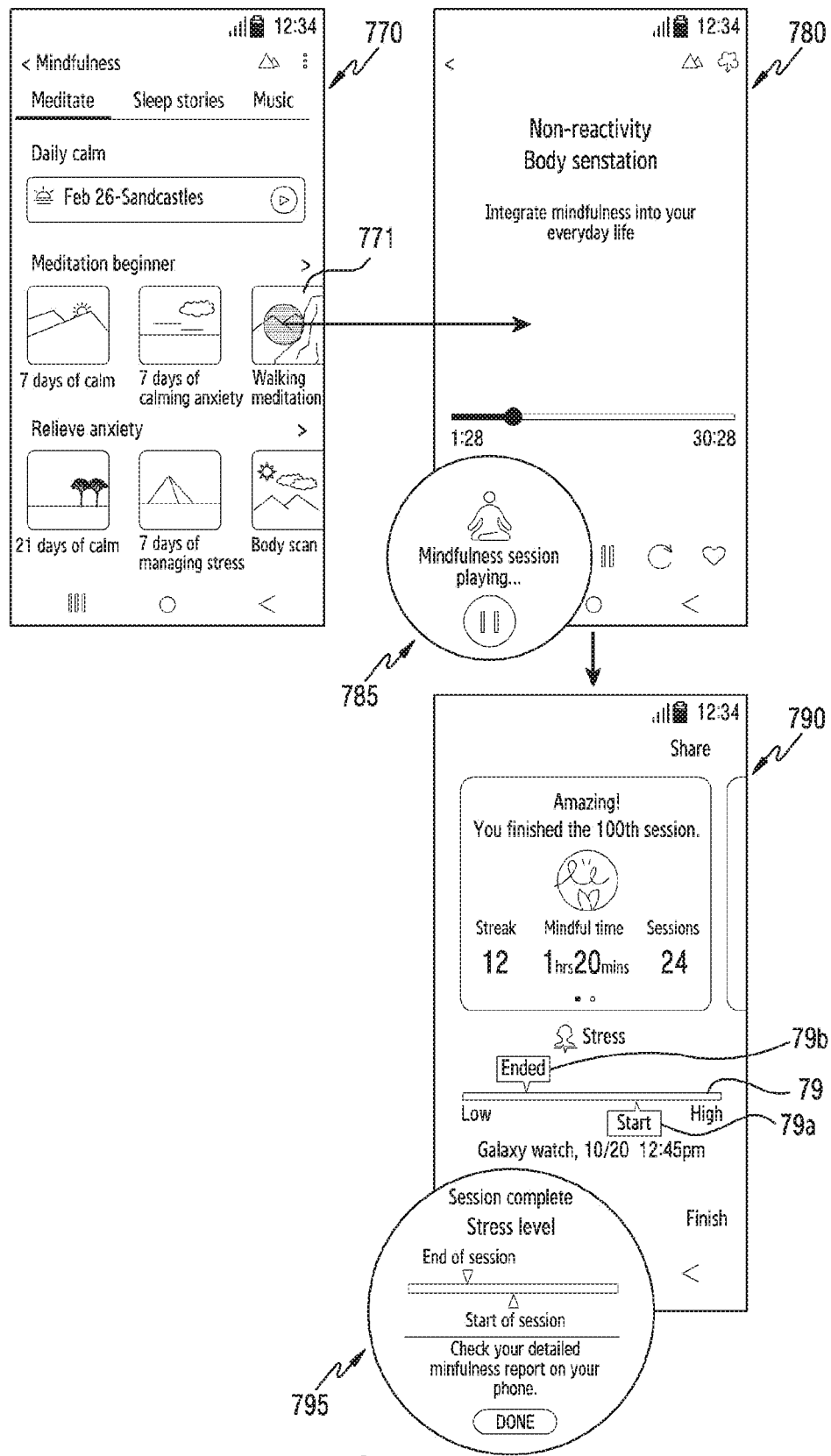
FIG. 7H is a diagram of an example of providing information for stress relief by an electronic device, according to an embodiment.

When it is determined that stress has occurred, the electronic device may provide a meditation list on a screen as shown in the drawing of reference numeral 770 of FIG. 7H. The meditation list may include types of meditation arranged in a sequence in which a type showing a larger degree of stress reduction precedes a type showing a smaller degree thereof. The meditation list may be changed according to users since the list reflects individual stress history data.

When a specific meditation 771 is selected in the meditation list, the electronic device may provide a meditation guide screen as shown in the drawing of reference numeral 780. Meanwhile, when the electronic device is a smart watch, the meditation guide screen may be provided as shown in reference numeral 785.

When the meditation is completed, the electronic device may provide a meditation completion screen as shown in the drawing of reference numeral 790. The meditation completion screen may include a bar graph 79 indicating a stress level 79a before the meditation and a stress level 79b after the meditation. Meanwhile, when the electronic device is a smart watch, the meditation completion screen may be provided as shown in reference numeral 795.

Figure 8:
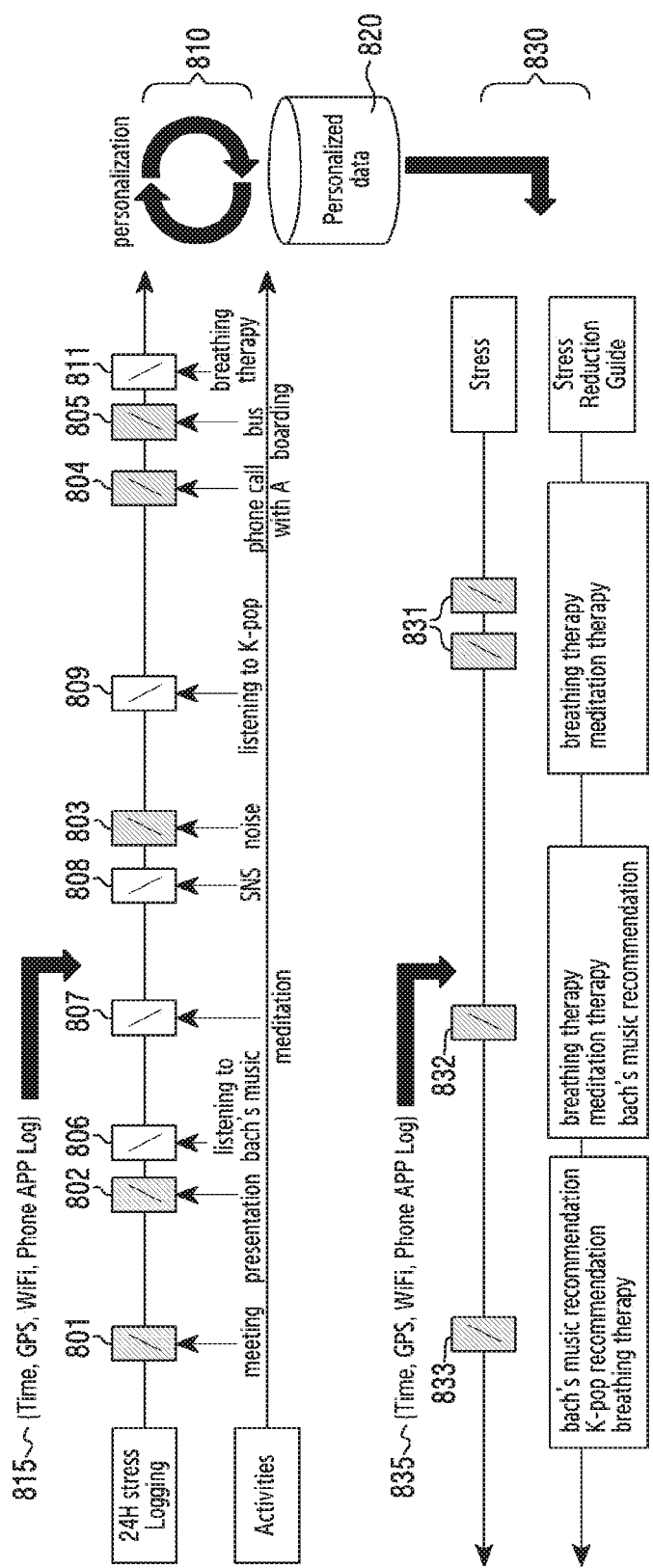
FIG. 8 is a diagram of an example of providing information for stress history management and stress relief by an electronic device, according to an embodiment.

FIG. 8 is a diagram of an example of providing information for stress history management and stress relief by an electronic device, according to an embodiment.

Referring to FIG. 8, an electronic device may continuously or periodically measure stress to manage a stress history together with contextual information 815. Referring to FIG. 8, it can be seen that stress has occurred during activities of a meeting 801, a presentation 802, noise 803, a phone call with A 804, and bus boarding 805, and that stress has been reduced (or relieved) during listening to Bach's music 806, meditation 807, social network service (SNS) 808, listening to K-pop 809, and breathing therapy 811. As such, through stress history information collected periodically or continuously, the electronic device may perform personalization 810 to generate personalized data 820. The stress history information collected through the electronic device may be collected and managed by an external electronic device (e.g., the stress history management server), and the personalization 810 and the generation of the personalized data 820 may also be performed by the external electronic device.

The stress may be measured through a device which is always worn by a user, such as a wearable device (e.g., the second electronic device 220), and the contextual information may be collected through another electronic device (e.g., the first electronic device 210 or an IoT device). When stress occurrence is detected through at least one sensor, the wearable device may notify the electronic device (e.g., the first electronic device 210) of the stress occurrence. The electronic device having received the notification of the stress occurrence may collect contextual information through at least one sensor and/or a log record, and map and store the collected contextual information and the stress occurrence. The electronic device may further receive contextual information from at least one IoT device connected through communication. As such, the measurement of stress and the collection of the contextual information may be performed by other electronic devices, and information (or data) measured or collected by other electronic devices may be integrated by one electronic device (e.g., the first electronic device 210, the second electronic device 220, or the stress history management server), and managed as useful information (stress history information).

The electronic device may guide a stress relief method when stress occurs, based on the personalized data 820 and contextual information 835. Based on the personalized data 820 and the contextual information 835, the electronic device may recommend a breathing therapy and a meditation therapy at the time of detecting occurrence of a first stress 831, recommend a breathing therapy, a meditation therapy, and Bach's music at the time of detecting occurrence of a second stress 832, and recommend Bach's music, K-pop, and a breathing therapy at the time of detecting occurrence of a third stress 833.

The stress may be measured through a device which is always worn by a user, such as a wearable device (e.g., the second electronic device 220), and the contextual information may be collected through another electronic device (e.g., the first electronic device 210 or an IoT device). When stress occurrence is detected through at least one sensor, the wearable device may notify the electronic device (e.g., the first electronic device 210) of the stress occurrence. The electronic device having received the notification of the stress occurrence may collect contextual information through at least one sensor and/or a log record, and may guide an appropriate stress relief method, based on the collected contextual information. The electronic device may transmit the collected contextual information to an external electronic device (e.g., the stress history management server), and receive a stress relief method from the external electronic device.

Figure 9:
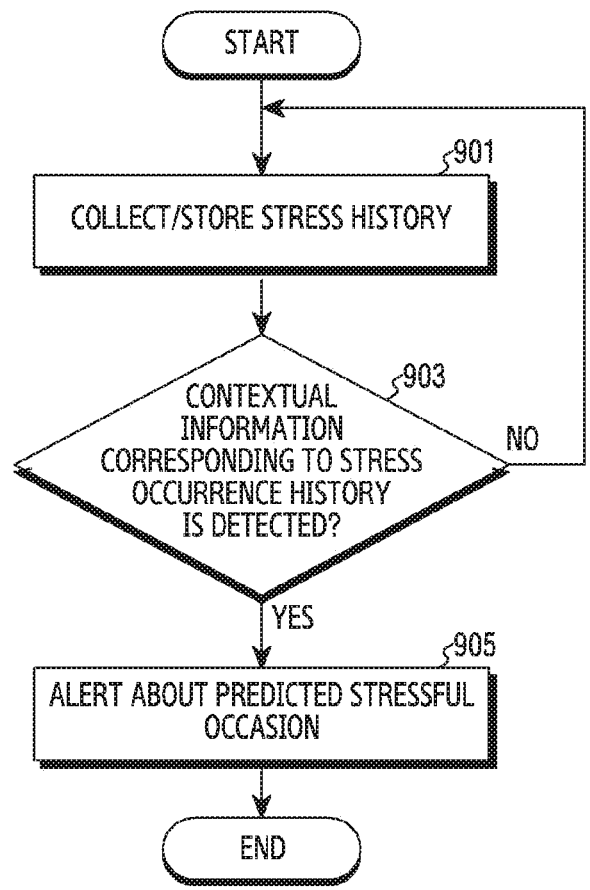
FIG. 9 is a flowchart of a method for predicting a stressful occasion and providing an alarm by an electronic device, according to an embodiment.

FIG. 9 is a flowchart of a method for predicting a stressful occasion and providing an alarm by an electronic device, according to an embodiment.

Referring to FIG. 9, at step 901, a processor of an electronic device may collect and store a stress history. The processor may measure stress periodically or continuously and store a result of the measurement. In addition, when stress satisfies a designated condition (when stress occurs), the processor may obtain contextual information and store the contextual information together.

At step 903, the processor may determine whether contextual information corresponding to a stress occurrence history is detected. The processor periodically may collect contextual information, and determine whether contextual information corresponding to the collected contextual information is included in the stress occurrence history. When the current time indicates 9 A.M. and a user is in a company, the processor may determine whether there is a stress history including contextual information of 9 A.M. and the company. The processor may determine whether there is a stress history including contextual information in a predetermined range (e.g., 1 hour or 1 km) from a current time and place. This is to alert a user to a stressful occasion in advance.

As a result of the determination of step 903, when the contextual information corresponding to the stress occurrence history is not detected, the processor may return to step 901 and repeat the above steps. On the other hand, as a result of the determination of step 903, when the contextual information corresponding to the stress occurrence history is detected, at step 905, the processor may alert that stress is expected. The processor may output, on a display, a pop-up message informing that stress is expected, or output, through a speaker, a sound effect or voice informing that stress is expected.

The processor may provide information (e.g., tea, music, meditation, or breathing) which can help to prepare for an expected stressful occasion.

An electronic device may include a user interface, at least one sensor, at least one processor operatively connected to the user interface and the at least one sensor, and a memory operatively connected to the processor. The memory stores instructions to, when executed, cause the at least one processor to collect stress-related information through at least a part of the at least one sensor, identify contextual information of a user when stress calculated based on the collected stress-related information satisfies a designated condition, and guide at least one of a plurality of stress relief methods through the user interface at least based on the identified contextual information.

The instructions, when executed, may further cause the at least one processor to determine the contextual information based on at least one of a time, a place where the electronic device is located, and an occasion.

The electronic device may further include a communication module for connecting to an external electronic device by wire or wirelessly, and the occasion may include at least one of information on an application being executed, information on content being executed, the type of the external electronic device connected through the communication module, and movement information of the user obtained by the at least one sensor.

The instructions, when executed, may further cause the at least one processor to obtain biometric information through the at least one sensor, calculate a stress value based at least in part on the obtained biometric information, and when the number of times by which the calculated stress value exceeds a first threshold exceeds a second threshold, determine that the designated condition is satisfied.

The at least one sensor may further include a biometric sensor and/or an image sensor, and the instructions, when executed, may further cause the at least one processor to obtain a bio-signal through the biometric sensor and collect the biometric information based on the obtained bio-signal, or to obtain a facial image of the user through the image sensor, extract a pulse wave signal from the facial image, and collect the biometric information, based on the extracted pulse wave signal.

The instructions, when executed, may further cause the at least one processor to transmit the stress relief method to a first external electronic device which is connected by wire or wirelessly through the communication module.

The instructions, when executed, may further cause the at least one processor to receive and collect the stress-related information from a second external electronic device connected through the communication module.

The instructions, when executed, may further cause the at least one processor to guide the stress relief method and then determine whether a stress value of the user changes, and give a weight to the stress relief method based on the change in the stress value.

The instructions, when executed, may further cause the at least one processor to periodically measure the stress of the user and store, in the memory, a stress history to which the measured stress and contextual information at the time of occurrence of the stress are mapped, and further reflect the stress history having a weight given thereto and guide at least one of the plurality of stress relief methods.

The instructions, when executed, may further cause the at least one processor to, in response to detection of the contextual information corresponding to the stress history by the at least one sensor, predict stress occurrence, alert about a predicted stressful occasion, and guide information helpful to the predicted stressful occasion through the user interface A method for providing information for stress relief by an electronic device may include collecting stress-related information through at least a part of at least one sensor, determining whether stress calculated based on the collected stress-related information satisfies a designated condition, identifying contextual information of a user in response to satisfying of the designated condition, and guiding at least one of a plurality of stress relief methods through a user interface at least based on the identified contextual information.

Identifying the contextual information may further include determining the contextual information, based on at least one of a time, a place where the electronic device is located, and an occasion.

The occasion may include at least one of information on an application being executed, information on content being executed, the type of an external electronic device connected through a communication module, and movement information of the user obtained by the at least one sensor.

Determining whether the stress satisfies the designated condition may further include obtaining biometric information through the at least one sensor, calculating a stress value based at least in part on the obtained biometric information, determining whether the calculated stress value exceeds a first threshold, in response to exceeding of the first threshold, determining whether the number of times by which the calculated stress value exceeds the first threshold exceeds a second threshold, and in response to exceeding of the second threshold, determining that the stress satisfies the designated condition.

Obtaining the biometric information may further include at least one of obtaining a bio-signal through a biometric sensor and collecting the biometric information based on the obtained bio-signal, obtaining a facial image of the user through an image sensor, extracting a pulse wave signal from the facial image, and collecting the biometric information based on the extracted pulse wave signal, and receiving the biometric information from an external electronic device connected through the communication module, and collecting the biometric information.

Guiding the stress relief method may include transmitting the stress relief method to the external electronic device through the communication module.

The method may further include guiding the stress relief method and then determining whether a stress value of the user changes; and giving a weight to the corresponding stress relief method, based on the change in the stress value.

The method may further include periodically measuring the stress of the user and storing, in a memory, a stress history to which the measured stress and contextual information at the time of occurrence of the stress are mapped.

Guiding may further include further reflecting the stress history having a weight given thereto and selecting at least one of the plurality of stress relief methods.

The method may further include determining whether the contextual information corresponding to the stress history is detected by at least one sensor, in response to detection of the contextual information corresponding to the stress history, predicting stress occurrence and alerting about a predicted stressful occasion, and guiding information helpful to the predicted stressful occasion.

The term "module" used herein may represent, for example, a unit including one or more combinations of hardware, software and firmware. The term "module" may be interchangeably used with the terms "logic", "logical block", "part" and "circuit". The "module" may be a minimum unit of an integrated part or may be a part thereof. The "module" may be a minimum unit for performing one or more functions or a part thereof. For example, the "module" may include an ASIC.

Various embodiments of the present disclosure may be implemented by software including an instruction stored in a machine-readable storage media readable by a machine (e.g., a computer). The machine may be a device that calls the instruction from the machine-readable storage media and operates depending on the called instruction and may include the electronic device. When the instruction is executed by the processor, the processor may perform a function corresponding to the instruction directly or using other components under the control of the processor. The instruction may include a code generated or executed by a compiler or an interpreter. The machine-readable storage media may be provided in the form of non-transitory storage media. Here, the term "non-transitory", as used herein, is a limitation of the medium itself (i.e., tangible, not a signal) as opposed to a limitation on data storage persistency.

A method according to various embodiments disclosed in the present disclosure may be provided as a part of a computer program product. The computer program product may be traded between a seller and a buyer as a product. The computer program product may be distributed in the form of machine-readable storage medium (e.g., a compact disc read only memory (CD-ROM)) or may be distributed only through an application store (e.g., a Play Store™). In the case of online distribution, at least a portion of the computer program product may be temporarily stored or generated in a storage medium such as a memory of a manufacturer's server, an application store's server, or a relay server.

Each component (e.g., the module or the program) according to various embodiments may include at least one of the above components, and a portion of the above sub-components may be omitted, or additional other sub-components may be further included. Alternatively or additionally, some components may be integrated in one component and may perform the same or similar functions performed by each corresponding component prior to the integration. Operations performed by a module, a programming, or other components according to various embodiments of the present disclosure may be executed sequentially, in parallel, repeatedly, or in a heuristic method. Also, at least some operations may be executed in different sequences, omitted, or other operations may be added.

While the disclosure has been shown and described with reference to certain embodiments thereof, it will be understood by those skilled in the art that various changes in form and details may be made therein without departing from the scope of the disclosure. Therefore, the scope of the disclosure should not be defined as being limited to the embodiments, but should be defined by the appended claims and equivalents thereof.

What is claimed is:

1. An electronic device comprising:
   communication module configured to communicate to an external electronic device by wire or wirelessly;
   at least one sensor comprising at least one biometric sensor;
   at least one processor operatively connected to the at least one sensor; and
   a memory operatively connected to the at least one processor,
   wherein the memory stores instructions to, when executed, cause the at least one processor to:
   collect stress-related information through at least a part of the at least one biometric sensor;
   identify contextual information of a user when a stress value calculated based on the collected stress-related information satisfies a designated condition, wherein the contextual information comprises a type of the external electronic device communicatively connected with the electronic device;
   at least partially based on the type of the external electronic device, determine a stress relief method from among a plurality of stress relief methods related to the stress-related information; and
   guide the determined stress relief method through the external electronic device.

2. The electronic device of claim 1, wherein the instructions, when executed, further cause the at least one processor to determine the contextual information based on at least one of a time, a place where the electronic device is located, or an occasion comprising the type of the external electronic device communicatively connected with the electronic device.

3. The electronic device of claim 2,
   wherein the occasion comprises at least one of information on an application being executed, information on content being executed, or movement information of the user obtained by the at least one sensor.

4. The electronic device of claim 1, wherein the instructions, when executed, further cause the at least one processor to obtain biometric information through the at least one sensor; calculate the stress value, based at least in part on the obtained biometric information; and, when a number of times by which the calculated stress value exceeds a first threshold exceeds a second threshold, determine that the designated condition is satisfied.

5. The electronic device of claim 4, wherein the at least one sensor further comprises an image sensor, and
   wherein the instructions, when executed, further cause the at least one processor to obtain a bio-signal through the at least one biometric sensor and collect the biometric information based on the obtained bio-signal, or to obtain a facial image of the user through the image sensor, extract a pulse wave signal from the facial image, and collect the biometric information based on the extracted pulse wave signal.

6. The electronic device of claim 1, wherein the instructions, when executed, further cause the at least one processor to transmit the determined stress relief method to a first external electronic device connected by wire or wirelessly through the communication module.

7. The electronic device of claim 6, wherein the instructions, when executed, further cause the at least one processor to receive and collect the stress-related information from a second external electronic device connected through the communication module.

8. The electronic device of claim 1, wherein the instructions, when executed, further cause the at least one processor to guide the determined stress relief method and then determine whether a stress value of the user changes; and give a weight to the stress relief method based on a change in the stress value.

9. The electronic device of claim 1, wherein the instructions, when executed, further cause the at least one processor to periodically measure the stress value of the user and store, in the memory, a stress history to which the measured stress value and contextual information at a time of occurrence of mapping the stress; and further reflect the stress history having a weight given thereto and guide at least one stress relief method of the plurality of stress relief methods.

10. The electronic device of claim 9, further comprising a display,
wherein the instructions, when executed, further cause the at least one processor to, in response to detection of the contextual information corresponding to the stress history by the at least one sensor, predict stress occurrence, alert about a predicted stressful occasion, and guide information helpful to the predicted stressful occasion through the display.

11. A method for providing information for stress relief by an electronic device, the method comprising:
collecting stress-related information through at least a part of at least one sensor; comprising at least one biometric sensor;
determining whether stress value calculated based on the collected stress-related information satisfies a designated condition;
identifying contextual information of a user in response to satisfying the designated condition, wherein the contextual information comprises a type of an external electronic device communicatively connected with the electronic device;
at least partially based on the type of the external electronic device, determining a stress relief method from among a plurality of stress relief methods related to the strew-related information; and
guiding of the determined stress relief method through the external electronic device.

12. The method of claim 11, wherein identifying the contextual information comprises determining the contextual information based on at least one of a time, a place where the electronic device is located, or an occasion comprising the type of the external electronic device communicatively connected with the electronic device.

13. The method of claim 12, wherein the occasion comprises at least one of information on an application being executed, information on content being executed, or movement information of the user obtained by the at least one sensor.

14. The method of claim 11, wherein determining whether the stress value satisfies the designated condition comprises:
obtaining biometric information through the at least one sensor;
calculating the stress value based at least in part on the obtained biometric information;
determining whether the calculated stress value exceeds a first threshold;
in response to the calculated stress value exceeding of the first threshold, determining whether a number of times by which the calculated stress value exceeds the first threshold exceeds a second threshold; and
in response to the number of times exceeding of the second threshold, determining the stress satisfies the designated condition.

15. The method of claim 14, wherein obtaining the biometric information comprises at least one of:
obtaining a bio-signal through the at least one biometric sensor and collecting the biometric information, based on the obtained bio-signal;
obtaining a facial image of the user through an image sensor, extracting a pulse wave signal from the facial image, and collecting the biometric information based on the extracted pulse wave signal; and
receiving and collecting the biometric information from a first external electronic device connected through a communication module of the electronic device.

16. The method of claim 11, wherein guiding the stress relief method comprises transmitting the determined stress relief method to the external electronic device through a communication module of the electronic device.

17. The method of claim 11, further comprising:
guiding the stress relief method and then determining whether the stress value of the user changes; and
giving a weight to the corresponding stress relief method based on a change in the stress value.

18. The method of claim 11, further comprising:
periodically measuring stress of the user and storing, in a memory, a stress history to which the measured stress value and contextual information at a time of occurrence of mapping the stress.

19. The method of claim 18, wherein guiding the at least one of a plurality of stress relief methods comprises further reflecting the stress history having a weight given thereto, and selecting at least one stress relief method of the plurality of stress relief methods.

20. The method of claim 18, further comprising:
determining whether the contextual information corresponding to the stress history is detected by the at least one sensor;
in response to detection of the contextual information corresponding to the stress history, predicting stress occurrence and alerting about a predicted stressful occasion; and
guiding information helpful to the predicted stressful occasion.

* * * * *